(12) United States Patent
Han et al.

(10) Patent No.: US 6,193,977 B1
(45) Date of Patent: Feb. 27, 2001

(54) PHARMACEUTICAL COMPOSITION COMPRISING AN AQUEOUS EXTRACT OF A MIXTURE OF *ANEMARRHENA* RHIZOMA AND PHELLODEDRON BARK FOR ANALGESIC AND ANTI-INFLAMMATION

(75) Inventors: Young-Bok Han; Eun-Kyung Hong; Young-Shin Chung; Sung-Jin Kim; Kyung-Yung Lee; Young-Lok Shin, all of Seoul (KR)

(73) Assignee: Medvill Co., Ltd., Seoul (KR)

( * ) Notice: Subject to any disclaimer, the term of this patent is extended or adjusted under 35 U.S.C. 154(b) by 0 days.

(21) Appl. No.: 09/524,880

(22) Filed: Mar. 14, 2000

(30) Foreign Application Priority Data

Mar. 18, 1999 (KR) .................................................. 99-9079

(51) Int. Cl.⁷ .................................................. A61K 65/00
(52) U.S. Cl. .......................................................... 424/195.1
(58) Field of Search .......................................... 424/195.1

(56) References Cited

U.S. PATENT DOCUMENTS 5,244,622 * 9/1993 Han et al. ......................... 424/195.1

FOREIGN PATENT DOCUMENTS

| | | | |
|---|---|---|---|
| JP56-040609 | 4/1981 | (JP) . | |
| JP63-054324 | 3/1988 | (JP) . | |
| JP1-128933 | 5/1989 | (JP) . | |
| JP2-180839 | 7/1990 | (JP) . | |
| JP2-311420 | 12/1990 | (JP) . | |
| JP7-242534 | 9/1995 | (JP) | ................. A61K/7/50 |
| 0196622 * | 3/1996 | (JP) | ................. 424/195.1 |
| JP10-236944 | 9/1998 | (JP) | ................. A61K/9/06 |
| JP11-049686 | 2/1999 | (JP) | ................. A61K/35/78 |

* cited by examiner

*Primary Examiner*—Jon P. Weber
*Assistant Examiner*—Patricia D Patten
(74) *Attorney, Agent, or Firm*—Sheridan Ross P.C.

(57) ABSTRACT

The present invention is directed to a pharmaceutical composition comprising an extract of a mixture of Anemarrhena Rhizoma, a member of the family Liliaceae and, Phellodendron bark, a member of the family Rutaceae that produces analgesic and anti-inflammatory effects, and its preparing method. The present invention is applicable to act on inflammation and pain, for example, chronic gastritis, arthralgia, benign prostate hyperplasia, chronic and recurrent cystitis, cervical disc, degenerative joint arthritis, rheumatoid arthritis, tennis elbow, osteoportotic pain, migraine, diabetic neuropathy pain, right flank pain, etc. The present invention a crude extract suitable for long-period administration with less side effects. Also, the present invention does not lead to dependency or resistance.

11 Claims, 11 Drawing Sheets

PHARMACEUTICAL COMPOSITION COMPRISING AN AQUEOUS EXTRACT OF A MIXTURE OF *ANEMARRHENA* RHIZOMA AND PHELLODEDRON BARK FOR ANALGESIC AND ANTI-INFLAMMATION

BACKGROUND OF THE INVENTION

1. Field of the Invention

The present invention relates generally to a pharmaceutical composition comprising aqueous extracts of Anemarrhena Rhizoma, a member of the family Liliaceae, and Phellodendron Bark, a member of the family Lilium for analgesic and anti-inflammation, and its preparing method. More particularly, it relates to a pharmaceutical composition comprising mixed aqueous extracts of Anemarrhena Rhizoma and Phellodendron Bark for analgesic and anti-inflammation against chronic gastritis, arthralgia, benign prostate hyperplasia, chronic and recurrent cystitis, cervical disc, degenerative joint arthritis, rheumatoid arthritis, tennis elbow, osteoportotic pain, migraine, diabetic neuropathy pain, Rt. flank pain, etc.

2. Description of the Related Art

There are two types of pain, one of which is fast pain sensed immediately in response to stimulants and the other is slow pain sensed gradually. The slow pain results from injuries to both the skin and the internal tissue and lasts long, while the fast pain results from injuries to the skin rather than to the internal tissue. The pain is sensed through receptors distributed over the skin and tissue, especially, those for mechanical, thermal and chemical stimulants. Upon receipt of stimulation, the receptors transmit sensation to the central nerve system. Examples of the chemicals exciting the chemical type of pain receptors include bradykinin, potassium ions, acids, proteolytic enzymes, etc. Compared to the other types of sensation, the lasting pain becomes more sensitive to stimulants and develops intolerance even to a weak stimulant.

In the body system, neurons of the brain and the vertebral column secrete those substances such as morphine that elicit an analgesic effect, and regulate the pain. Examples of the analgesic substances include endorphin, enkephalin and dynorphin secreted from the brain, and serotonin and enkephalin from the vertebral column.

The existing analgesics may be classified into two categories: (a) narcotic analgesics, e.g., codeine and dihydrocodeine and (b) non-steroidal anti-inflammatory drugs (NSAIDSs), e.g., aspirin, ibuprofen and indomethacin.

The narcotic analgesics excite receptors of the central nerve system to alleviate both light and severe pains. The narcotic analgesics are used in an increased dose depending on the degree of a pain and very effective in pain relief. However, the effect of the narcotic analgesics is practically dose-dependent and results in resistance to analgesics. In the worst cases, the narcotic analgesics adversely produce a side effect of depressing the respiratory and circulatory organs.

The NSAIDS inhibits the production of prostaglandin from arachidonic acid. Thus NSAIDS not only acts to alleviate pain and platelet agglutination attendant upon particular degenerative diseases but also reduces inflammation. The NSAIDS is to some extent effective as an analgesic and anti-inflammatory agent but often leads to side effects, i.e., stomach ulcer and bleeding of digestive organs.

Recently, there is an attempt to implement a therapeutic method that involves administration of a combination of narcotic analgesics and NSAIDs in order to maximize the beneficial effects of the above-mentioned single components while avoiding the side effects thereof.

Meanwhile, inflammation refers to a response to an tissue injury caused by pathogenic microorganisms, trauma, chemicals and heat in view of restoring the injured tissue, that is, the whole local tissue response to an injury involving secretion of several mediators from the injured tissue, induction of immunocytes and recovery of the injured tissue. This process can be summarized as follows. With tissue cells damaged or destroyed, acids and chemical mediators are released. The mediators cause the dilation of blood capillaries and increase their permeability. Histamine secreted from mast cells or basophiles initiates the response of blood vessels, and serum kinin produced from alpha-2-globulin of blood serum mediates the long-acting response of blood vessels through the blood coagulation mechanism. The blood capillary dilation increases the blood flow, and causes heat and redness. The increased permeability of the blood capillaries cause blood cells, proteins and fluids to exude into surrounding tissues, leading to swelling. Such exudation can accelerate further destruction of cells, and the increased blood pressure stimulates peripheral nerves to cause pain. The pain increases due to secretion of kinin and acids. Other mediators secreted from the tissue include serotonin, prostaglandin, reactants of the complement system, and lymphokine secreted from T-cells.

As fluid exudes from the capillaries, leukocytes (i.e., neutrophils and monocytes) migrate to the damaged region and digest or dissolve inflammation-causing substances to recover the damaged area. Another important cells in the inflammatory reaction are monocyte-originated macrophages that also participate in phagocytosis and rapidly proliferate when the tissue is damaged. Fusion of the macrophages or amitotic division of large fragments produces giant cells.

The inflammatory reaction occurs locally or entirely in the body system. In some cases, pyrogens secreted from bacteria stimulate the thermoregulatory center in the brain and produce a fever which, in turn, raises metabolic rate, decreases appetite and results to depletion of somatic tissue with muscle and body fat. Fluid losses may result in dehydration. Lymph fluid absorbs fluid and the protein exuded from the blood capillaries, and transports them to the lymphnode, which causes lymphadenitis characterized by lymphnode enlargement and pain.

As described, inflammation is a primary mechanism of the body system to repair tissue damage or protect against latent infection. However, an untimely or chronic inflammation reaction can result in pain or diability.

There can be used two types of antiinflammatory medications, the one of which involves inhibiting production and exudation of inflammatory cells and the other involves reducing secretion of inflammation mediators. The currently used medical agents may be divided into NSAIDs, capable of producing both analgesic and inflammatory effects as described above, and steroidal anti-inflammatory drugs. The NSAIDs are widely spread as analgesic and inflammatory agents and have a mechanism of inhibiting production of prostaglandin from arachidonic acid. Corticosteroids used against inflammation not only inhibit generation of prostaglandin but also act on beta-adrenergic receptors of leukocytes to inhibit secretion of inter-leukins (ILs) and reduce permeability of the blood vessels, which in turn inhibits exudation of blood and inflammatory cells. Despite the therapeutic effects, corticosteroids have been reported to produce a number of side effects, such as increasing the size of erythrocytes, weight gain, accelerating progression of osteoporosis and weakening blood capillary, raising blood pressure and stomach ulcer. Cromolyn sodium is also used as an inflammatory agent involving stabilization of the cytoplasmic membrane of mast cells and inhibiting activation of macrophages, but produce a number of side effects.

The following description deals with two cases of benign prostate hyperplasia and chronic cystitis in detail.

Benign prostate hyperplasia(BPH) is one of the prevailing diseases among at least 50% of aged males over fifty and estimated as a degenerative disease involving the enlargement of prostate gland due to intact androgen supply as the man gets old. In the early stage of forties, nodules can generate in the transition(grandula) and periurethral zones (stromal). The nodules formed in the transition zone continuously grow into the major part of the main mass of the BPH, in which case the central and peripheral zones are compressed and fibromuscular tissue develops between the BPH tissue. This progresses over several years and symptoms appear as the enlarged prostate obstructs the urinary track.

The symptoms of benign prostate hyperplasia can be divided into "obstructive" symptoms caused by obstruction of the urethra with BPH, and "irritative" symptoms caused by inflammation or infection of the urinary track. The obstructive symptoms include weak stream, straining, prolonged micturition, postmicturitional dribbling, urinary retention and paradox incontinence. The irritative symptoms include urgency, frequency, nocturia, urge incontinence and suprapubic pain. The irritative symptoms are usually accompanied with infection and the patient suffering from these irritative symptoms is hard to be satisfied even after a prostatectomy.

The recent therapies of benign prostate hyperplasia such as prostatectomy or removal of the dilative prostate using a laser beam are a temporary treatment that cannot inhibit lasting dilation of the prostate. Therapeutic drugs used against benign prostate hyperplasia are alpha-adrenergic antagonists inhibiting tone of the prostate or reducing androgen hormones production to prevent prostate dilation, but cannot be used in a continuous manner due to side effects.

On the other hand, chronic cystitis is a quite common disease to menopausal and post-menopausal women, and primarily caused by viruses and stress. This disease has limitations on the treatment because it is easy to become chronic and recur. Chronic cystitis is accompanied with symptoms similar to those of benign prostate hyperplasia, i.e., frequency, nocturia, urge incontinence, and so forth. In most cases, trimethoprime-sulfaethoxazol (4 single-strength tablets) and fluoroquinoline (norflxacin, ciprofloxacin, ofloxacin) are used for treatment of acute cystitis free from a complication, caused by infection of *E. coli*. Chronic or recurrent cystitis or urinary track infection with complications (including cystitis) usually result from infection through *E. coli*, Klebsiella, Proteus, Pseudomonas, etc. Because most these infective viruses are antibiotic-resistant strains, a long-term treatment is required using antibiotics or antibacterial agents such as imipenem, cephalosporine, aminoglycoside or ceftraxone. The related diseases are ready to recur after a long-term treatment, and hence not curable completely. The diseases also produce a number of side effects.

Trimethoprime-sulfaethoxazol is a widely used antibacterial agent with side effects involving skin rash, central nerve disorder, and an increased toxicity to blood picture, gastrointestinal system, liver and kidney. Fluoroquinoline is a quinoline-based fluoride and causes adverse side effects such as nausea, abdominal sickness, headache and vertigo and, for the worse, skin rash and photosensitization disease. Amorcsillin is a semi-synthetic aural penicillin antibiotic and produces side effects in order of fever, bronchospasm, serum sickness, exfoliative dermatitis, and anaphylaxis. Cephalosporine is a relatively less toxic, antibiotic derived from a fungus called *Cephalosporium acremonium* and, when administered as a parenteral preparation, causes local pain and thrombophlebitis and produces toxicity to the kidney. Imipenem is a sort of β-lactam that usually causes nausea, vomiting, and often, seizures and CNS lesions. Aminoglycoside comprises a combination of different antibiotics isolated from the genus Streptomyces (except for gentamycin isolated from *Micromonospora purpurea*). All aminoglycoside antibiotics having a narrow safety margin lead to disorder in protein synthesis of bacterium and hence bactericidal action, and usually give rise to adverse side effects including cytotoxicity such as tinnitus and deafness, vertigo and walking difficulty.

Since analgesic and inflammatory agents are not limited in their use to one disease only but widely used for various diseases, there is a need for study and development of a non-narcotic analgesic without any side effect, and a therapeutic drug having tissue specificity with less side effects.

SUMMARY OF THE INVENTION

It is, therefore, an object of the present invention to provide a pharmaceutical composition for analgesic and anti-inflammation, comprising the mixed aqueous extracts of Anemarrhena Rhizoma and Phellodendron Bark, that is suitable for long-period administration with less side effects, and its preparing method.

It is another object of the present invention to provide a non-narcotic pharmaceutical composition quite excellent in both analgesic and inflammatory effects without developing dependency or resistance, and its preparing method.

It is still another object of the present invention to provide a pharmaceutical composition quite excellent in both analgesic and inflammatory effects against benign prostate hyperplasia, chronic and recurrent gastritis, arthralgia, chronic gastritis and cervical disc.

The present invention is directed to a pharmaceutical composition comprising the mixed aqueous extracts of Anemarrhena Rhizoma and Phellodendron Bark for treatment of inflammation and pain. The mixed aqueous extracts of Anemarrhena Rhizoma and Phellodendron Bark have an anti-inflammatory effect specific to a peripheral tissue or a non-narcotic analgesic effect. The present invention is applicable to normal inflammation and pain, in particular, chronic gastritis, arthralgia, benign prostate hyperplasia, chronic and recurrent cystitis, cervical disc, degenerative joint arthritis, rheumatoid arthritis, tennis elbow, osteoporotic pain, migraine, diabetic neuropathy pain and Rt. Flank pain.

The pharmaceutical composition comprises the mixed aqueous extracts obtained from a mixture of Anemarrhena Rhizoma and Phellodendron Bark at a dry weight ratio of 1:0.2 to 1:5, preferably 1:0.5 to 1:2, more preferably 1:1.

The present invention is also directed to an anti-inflammatory and analgesic agent containing a therapeutic effective amount of the mixed aqueous extracts of Anemarrhena Rhizoma and Phellodendron Bark. In addition to the mixed aqueous extracts, the anti-inflammatory and analgesic agent may be formulated for pharmaceutical unit administration, with pharmaceutically acceptable carriers, excipients or diluting agents. Examples of unit formulation include a tablet, capsule, solution, suspension, syrup, beverage and injection. The mixed aqueous extracts of Anemarrhena Rhizoma and Phellodendron Bark can be formulated as an oral preparation in a daily dose of 10–50 mg/kg body weight of an adult. As described above, the mixed aqueous extracts can be extracted from Anemarrhena Rhizoma and Phellodendron Bark at a dry weight ratio of 1:0.2 to 1:5, preferably 1:0.5 to 1:2, more preferably 1:1.

The mixed aqueous extracts of Anemarrhena Rhizoma and Phellodendron Bark can be obtained by a method comprising the steps of: extracting the mixed plant materials of Anemarrhena Rhizoma and Phellodendron Bark with water and filtering the mixed extracts; saturating a filtrate under a high pressure to remove the coagulated proteins produced therein; adding an organic solvent to the filtrate to remove substances soluble in the organic solvent; and separating and lyophilizing an aqueous layer. Here, the water for extraction is added at a weight ratio of 1:10–45, preferably, 1:25–35 with respect to the mixed plant materials of Anemarrhena Rhizoma and Phellodendron Bark. The organic solvent as used herein can be chloroform or hexane.

BRIEF DESCRIPTION OF THE DRAWINGS

The above and other objects, features and advantages of the present invention will become more apparent from the following detailed description when taken in conjunction with the accompanying drawings in which.

DETAILED DESCRIPTION OF THE PREFERRED EMBODIMENT

Figure 1:
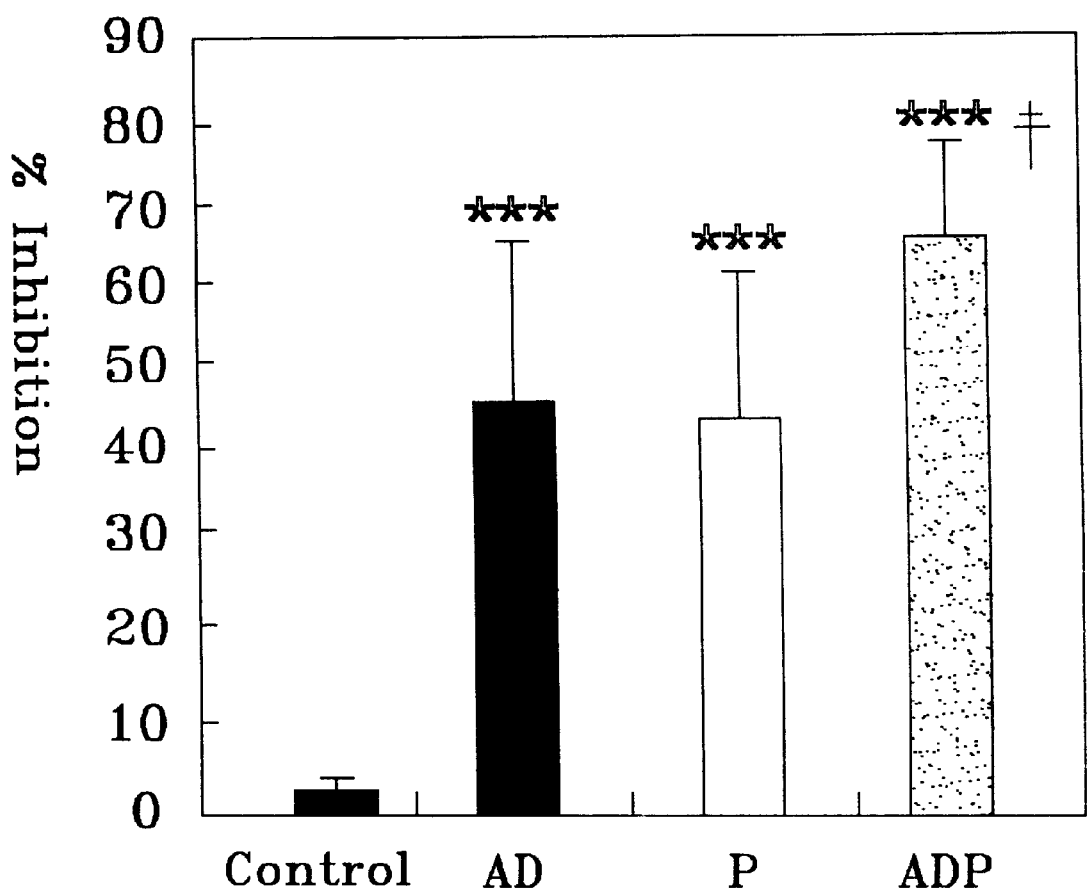
FIG. 1 shows anti-inflammatory effects of the present invention mixed aqueous extracts of Anemarrhena Rhizoma and Phellodendron Bark, and single extracts thereof.

A preferred embodiment of the present invention will be described below with reference to the accompanying drawings.

The plant used herein to prepare an aqueous extract in accordance with the present invention, Anemarrhena Rhizoma is a perennial grass indigenous to China that is cultivated at the central area in Korea. The present invention uses a dried rhizome of Anemarrhena Rhizoma, representatively, *Anemarrhena asphodelorides* BUNGE whose rhizome is reported to be effective for anti-inflammation, removal of fever, antidiarrhea, diuresis, antilumbago and sedation, according to pharmacopoeias (KP and JP). This medicinal plant contains 6% asphonins; steroid sapogenins, e.g., sarsasaponin and markogenin (2-hydroxy sarsasapogenin); flavonoids; and tannins. The Dongeui Bokam (Eastern Medical Handbook) and the Boncho Kangmok (Botanical List) state that Anemarrhena Rhizoma acts on "Goljeung Nohyeul", the meaning of which is chronic pain from osteoporosis occurring in the bone.

The other plant as used herein, Phellodendron Bark is the bark of Phellodendron trees indigenous to Korea, Japan and China. A representative Phellodendron tree is *Phellodendron amurense* RUPRECHT, the variants of which are var. *latifoliolatum* NAKAI, var. Japonicum OHWI, *P. insulare* NAKAI, *P. molle* NAKAI, and *P. sachalinense* Sarg. The Phellodendron Bark contains about 1.5–4.5% of aqueous alkaloids and yellow or yellowish brown pigments. The main constituent of the alkaloids is berberine. Besides, Phellodendron Bark has been reported to contain palmatine, magnoflorine, guanidine, jateorrizine, phellodendrine, candicine, menisperine and, as bitter substances, obakunone, obakulactone and β-sitosterol. The Boncho Kangmok and the Pharmacopoeia (Pharmacy) state that these components act on bone diseases and jaundice due to antibacterial, antihypertensive, central nerve inhibitory, acetylcoline increasing and anti-inflammatory effects. Phellodendron Bark also acts on typhoid and gastrointestinal disease, and the bark has been used as bitter stomachic, intestinal agent, and astringent anti-inflammatory agent against gastroenteritis, abdominal pain and jaundice.

Although the effectiveness of the individual plant is reported in regard to analgesic and inflammatory actions, it has not been reported that the mixed aqueous extracts obtained from the two plants produce much more remarkable analgesic and inflammatory effects with less side effects than single aqueous extracts, and that the mixed aqueous extracts have been used to act on benign prostate hyperplasia, cystitis, arthralgia, cervical disc, degenerative joint arthritis, rheumatoid arthritis, tennis elbow, osteoportotic pain, migraine, diabetic neuropathy pain, Rt. flank pain, etc.

The following description deals with an example of a method for preparing mixed aqueous extracts.

A first step involves pulverizing a mixture of dried Anemarrhena Rhizoma and Phellodendron Bark and subjecting the pulverized mixture to heat extraction using water or distilled water as a solvent under saturated vapor pressure (121° C., 15 pound/in$^2$). The amount of water is 10–45 weight parts preferably, 25–35 weight parts, based on 1 weight part of the mixture.

A second step involves subjecting the extracts to centrifugation to remove the residue, saturating the extracts again under high pressure, e.g., boiling the extracts in an autoclave under vapor pressure (121° C., 15 lb/in$^2$), to coagulate residual protein, and subjecting the extracts to centrifugation to remove the protein.

A third step involves subjecting the filtrate to extraction with an appropriate organic solvent such as chloroform, hexane, dichloromethane or cyclohexane, preferably, chloroform or hexane to remove impurities such as resin and fiber, purifying the aqueous phase using talc, and lyophilizing the purified extract to obtain the desired mixed aqueous extracts.

The present invention is first verified as a very safe drug in an acute toxicity test. The resulting mixed aqueous extracts of Anemarrhena Rhizoma and Phellodendron Bark obtained in the above method are found to have both analgesic and inflammatory effects. An experiment also reveals that the mixed aqueous extracts obtained by extracting the mixture of Anemarrhena Rhizoma and Phellodendron Bark with water are much superior in analgesic and inflammatory effects to single aqueous extracts obtained from the individual plants. The present invention is expected to have widespread application, for example, to benign prostate hyperplasia, chronic and recurrent cystitis, osteoportotic pain, migraine, diabetic neuropathy pain and Rt. Flank pain. Particularly, in case of prostatic diseases, the present invention is expected as a therapeutic agent for benign prostate hyperplasia because it inhibits dilation of the prostate and alleviates inflammation of the urinary track and dysuria, such that irritative symptoms ameliorate and obstruction mitigates gradually. It is shown that in the action mechanism, alpha-adrenergic receptors specifically distributed over the urinary track and the prostate may mediates a combination of anti-inflammatory and analgesic actions to enhance the therapeutic effect of the present invention.

A preparation of Anemarrhena Rhizoma and Phellodendron Bark may be administrated in a therapeutically effective amount either alone or with a pharmaceutically acceptable carrier, excipient or diluent in any mode of administration oral or parenteral such as intravenous, subcutaneous and intramuscular, or other suitable form well-known to the skilled in the art. A preparation of the present invention composition suitable for oral dosage may be in the form of, for example, a tablet, capsule, solution, suspension, syrup or beverage. Such a preparation comprising Anemarrhena Rhizoma and Phellodendron Bark for oral dosage may also be in the form of a sterile injectable liquid or a sterile parenteral injection such as oily suspension. The suspension may be prepared with an appropriate dispersing or suspending agent by a known method in the art. The sterile parenteral injection may be a sterile injection or suspension including a diluting agent or a solvent parenterally acceptable such as 1,3-butanediol. The acceptable diluting agents that may be employed are water, Ringer's solution and isotonic sodium chloride solution. In addition, sterile and fixed oils are conventionally as a solvent or suspending medium. Synthetic monoglycerides and diglycerides find use as fixed oils in the preparation of injectables.

Daily doses are variable depending on the severity of the disease, the sex, age and weight of the subject to be treated, and the effect to be accomplished. For oral administration to an adult person, the mixed extract may be administered in daily dosage in the range of about 5 to 50 mg per kg of body weigh, preferably 10–40 mg/kg body weight. For parenteral administration, the extract may be administered in a daily dose of 20–100 mg for a 60 kg adult.

The present invention will be described below in further detail with referent to the following examples, which illustrate but are not intended to limit the present invention.

EXAMPLE 1
Preparation of Mixed Extract

A mixture (1:1) of dried *Phellodendron amurense* RUPRECHT and Anemarrhena Rhizoma was first ground in a mill to collect 100 g of powder, which was subsequently saturated and extracted with 300 ml of water or distilled water at a temperature of 121° C. under the vapor pressure of 15 lb/in$^2$ for 40 to 60 minutes. With centrifugation, the water-soluble extract was separated from the residues. The supernatant was filtered and concentrated to be 1500 ml in total volume. The resulting filtrate was saturated with water at 121° C. under the vapor pressure of 15 lb/in$^2$ for 15 minutes to separate the filtrate into an aqueous solution and a solid, especially protein-containing residue. The deposit was removed by centrifugation and the aqueous solution was filtered to obtain a second filtrate, which was added to a fractional funnel. Then, 40 ml of chloroform was added to the filtrate to desolve resin and fiber and remove the chloroform phase. This procedure was repeatedly performed twice and 200 ml of n-hexane was added to the aqueous phase to remove the remaining protein, resin, fiber and soluble materials. The aqueous layer was collected and warmed to 60–80° C. After adding 500 g of talc, the mixture was agitated and vacuum was applied to filter talc. The resulting filtrate was then slowly filtered again, lyophilized and powdered. Thus an about 15000 mg aqueous extract was obtained with a yield of about 15% (dry weight %) from the mixture of *Phellodendron amurense* RUPRECHT and Anemarrhena Rhizoma.

EXAMPLE 2
Preparations Containing Mixed Aqueous Extracts

1. Tablets 250 mg of the freeze-dried, mixed extract powder of the present invention prepared in Example 1 was mixed with 260 mg of lactose as an excipient for direct tableting, 35 mg of avicel (microcrystalline cellulose), 15 mg of sodium starch glyconate as a disintegration adjuvant, and 80 mg of tableting low-hydroxypropylcellulose (L-HPC) in a U-shaped mixer for 20 min. 10 mg of magnesium stearate was then further added and mixed for 3 min. Through a quantitative test and a constant humidity test, the mixture was then tableted and film-coated to obtain tablets each containing 225 mg of the mixed extract.

2. Syrup

With a defined amount of white sugar dissolved in a defined amount of water, 80 mg of paraoxymethyl benzoate and 16 mg of paraoxypropyl benzoate were added as preservatives. Then, 4.5 g of the freeze-dried, mixed aqueous extract powder of the present invention prepared in Example 1 was added and completely dissolved in the sugar solution at 60° C. The resulting solution was then cooled and diluted with distilled water to be 150 ml in volume, thus obtaining 3% syrup.

3. Capsules 450 mg of the freeze-dried, mixed aqueous extract powder of the present invention prepared in Example 1 was mixed with 50 mg of lactose as a carrier. Hard gelatin capsules were then packed with the resulting mixture to obtain the present invention capsules.

4. Beverage 450 mg of the freeze-dried, mixed aqueous extract powder of the present invention prepared in Example 1 was dissolved in an appropriate amount of water. Then, there were added vitamin C as a supplemental component, citric acid, sodium citrate and high fructose syrup as corrigents, and sodium benzoate as a preservative. The resulting solution was diluted with water to be 100 ml in volume, thus obtaining a 0.45% composition for beverage.

5. Injection

The freeze-dried, mixed extract powder of the present invention prepared in Example 1 was dissolved in water for injection, Ringer's solution and physiological saline. The resulting solution passed through a membrane filter to obtain a sterile injection containing the mixed extract in a concentration of 3%.

EXAMPLE 3
Measurement of % Inhibition for Anti-inflammatory Effect of Mixed Extract Using Carrageenin Paw-Edema Method Seven (7) male Sprague Dawley(SD) rats of about 200 g in weight in a control group were given an injection of physiological saline. Each seven (7) male SD rats of the same weight in three experimental groups were administrated 100 mg/kg body weight (i.p.) of the mixed aqueous extracts of the present invention or the single plant extracts of *Phellodendron amurense* RUPRECHT and Anemarrhena Rhizoma. Immediately after administration, 0.1 ml of saline solution containing 1% carrageenin was hypodermically injected into the sole of the paw of all the rats. After one hour, the volumes of edemas formed up to the ankle of the rats were measured and applied to the following equation to calculate the value of % inhibition.

% inhibition=100(volume difference)drug/(volume difference)control×100

The results are presented in Table 1 and FIG. 1.

TABLE 1

Anti-inflammatory Effects of the Present Invention Mixed Aqueous Extracts and Single Extracts of *Phellodendron amurense* RUPRECHT and *Anemarrhena* Rhizoma

| Experimental Group | Dose (mg/kg) | Injection Route | % Inhibition |
|---|---|---|---|
| Control Group | 0.9% Saline | i.p. | 3 ± 1 |
| Single Aqueous Extract of A | 100 | i.p. | 44 ± 11.3*** |
| Single Aqueous Extract of B | 100 | i.p. | 43.5 ± 8.5*** |
| Mixed Aqueous Extracts of A and B | 100 | i.p. | 65 ± 9.2***,⊥ |

A: *Anemarrhena* Rhizoma
B: *Phellodendron amurense* RUPRECHT
***: Significantly different from the control group $p < 0.001$.
⊥: Significantly different from the single plant extracts $p < 0.05$
i.p.: intraperitoneal In FIG. 1, AD, P and ADP indicate the anti-edema effects of the single aqueous extracts of Anemarrhena Rhizoma and *Phellodendron amurense* RUPRECHT and the mixed aqueous extracts of the present invention, respectively. The mixed aqueous extracts of the present invention had a considerable anti-edema effect of 65%, with a significant difference $p < 0.001$ from the control group (3% inhibition) and $p < 0.05$ from the respective single extracts.

Example 4

Measurement of % Inhibition for Analgesic Effect of Mixed Aqueous Extracts Using Acetic Acid Writhing Method Seven (7) male mice of 20–25 g weight in a control group were given an injection of saline. Each seven (7) male mice of the same weight in three experimental groups are administrated 100 mg/kg body weight (i.p.) of the mixed aqueous extracts of the present invention or the single plant extracts of *Phellodendron amurense* RUPRECHT and Anemarrhena Rhizoma. After 30 min., 0.1 ml of 0.7% acetic acid solution was administered in a dose of 0.1 ml/10 g (body weight) by intraperitoneal injection. The number of writhings was then counted for 10 min. 10 minutes after administration and applied to the following equation to calculate the value of % inhibition.

Figure 2:
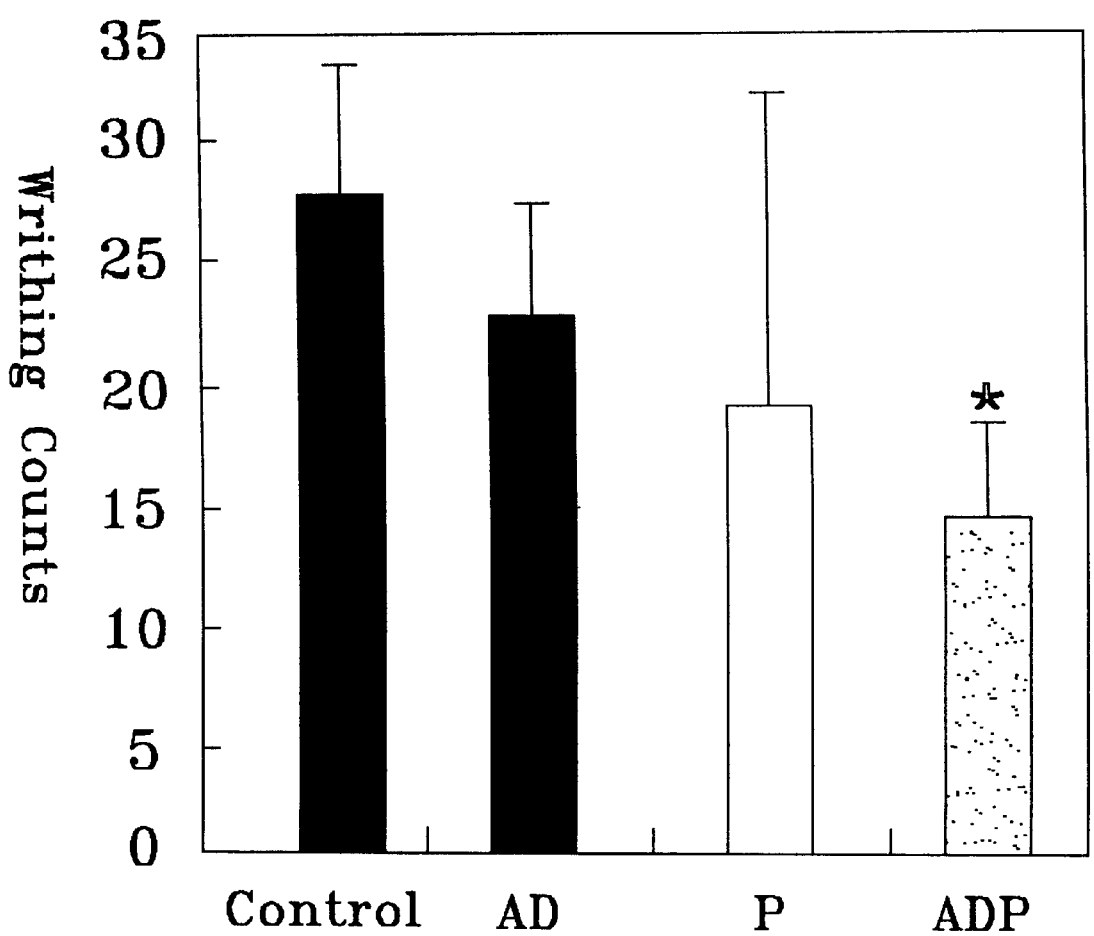
FIG. 2 shows analgesic effects of the present invention mixed aqueous extract of Anemarrhena Rhizoma and Phellodendron Bark, and single aqueous extracts thereof.

% inhibition=100×[(writhing counts)control−(writhing counts)drug]/(writhing counts)control The results are presented in Table 2 and FIG. 2.

TABLE 2

Analgesic Effects of the Present Invention Mixed Aqueous Extracts and Single Aqueous Extracts of *Phellodendron amurense* RUPRECHT and *Anemarrhena* Rhizoma by Acetic Acid Writhing Method.

| Experimental Group | Dose (mg/kg) | Injection Route | Writhing Counts | % Inhibition |
|---|---|---|---|---|
| Control Group | 0.9% Saline | i.p. | 27 ± 6 | |
| Single Aqueous Extract of A | 100 | i.p. | 22.5 ± 3.5 | 16.7 |
| Single Aqueous Extract of B | 100 | i.p. | 20 ± 12.5 | 25.9 |
| Mixed Aqueous Extracts of A and B | 100 | i.p. | 16 ± 3* | 40.7 |

A: *Anemarrhena* Rhizoma
B: Phellodendron amurense RUPRECHT
*: $p < 0.05$ in comparison with control
i.p.: intraperitoneal In FIG. 2, AD, P and ADP indicate the analgesic effects of the single aqueous extracts of Anemarrhena Rhizoma and *Phellodendron amurense* RUPRECHT and the mixed aqueous extracts of the present invention, respectively. The mixed aqueous extracts of the present invention had an analgesic effect of 40.7% with a significant difference $p < 0.05$ from the control. The single aqueous extracts from the two plants had an analgesic effect of 16.7% and 25.9%, respectively, with no significant difference from the control. This result demonstrates a synergistic effect of the mixed aqueous extracts from the two plants in terms of the increased analgesic effect, compared to the individual aqueous extracts.

EXAMPLE 5

Measurement of % Inhibition for Analgesic Effect of the Present Invention Mixed Aqueous Extracts Using Tail-Flick Method Seven (7) male SD rats of about 200 g in weight in a control group were given an injection of saline. Each seven (7) male rats of the same weight in three experimental groups were administrated 100 mg/kg body weight (i.p.) of the mixed aqueous extracts of the present invention or the single plant extracts of *Phellodendron amurense* RUPRECHT and Anemarrhena Rhizoma. After 30 min., the threshold was determined by measuring a latency required for the white rats to flick their tails out when shedding a high-density beam on the 2–5 cm part of the tails. A cutoff time was set to 10 seconds in view of avoiding damage of the tails. Then, the value of % inhibition was calculated using the following equation.

% inhibition=100×[(latency)drug−(latency)control]/[10−(latency)control]

Figure 3:
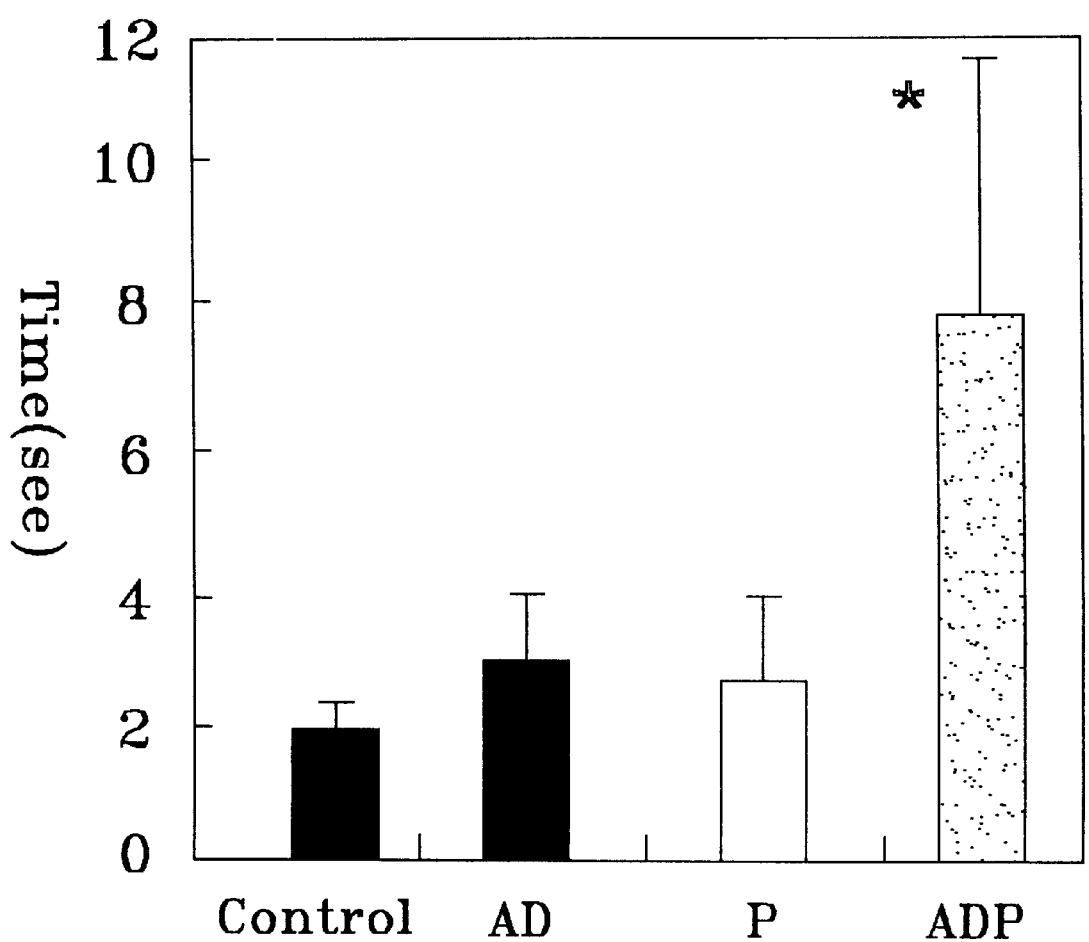
FIG. 3 shows analgesic effect of the present invention mixed aqueous extracts of Anemarrhena Rhizoma and Phellodendron Bark, and single aqueous extracts thereof in a tail-flick test.

The results are presented in Table 3 and FIG. 3.

TABLE 3

Analgesic Effects of the Present Invention Mixed Aqueous Extracts and Single Aqueous Extracts of *Phellodendron amurense* RUPRECHT and *Anemarrhena* Rhizoma by Tail-Flick Method.

| Experimental Group | Dose (mg/kg) | Injection Route | Writhing Counts | % Inhibition |
|---|---|---|---|---|
| Control Group | 0.9% Saline | i.p. | 2 ± 0.2 | |
| Single Aqueous Extract of A | 100 | i.p. | 2.9 ± 0.9 | 11.3 |
| Single Aqueous Extract of B | 100 | i.p. | 2.6 ± 1.0 | 7.5 |
| Mixed Aqueous Extracts of A and B | 100 | i.p. | 8 ± 3.8* | 75 |

A: *Anemarrhena* Rhizoma
B: *Phellodendron amurense* RUPRECHT
*: $p < 0.05$ in comparison with contol
i.p.: intraperitoneal In FIG. 3, AD, P and ADP indicate as in FIG. 2. The mixed aqueous extracts of the present invention had an analgesic effect of 75% with a statistic significant difference $p<0.05$ from the control. The single aqueous extracts had an analgesic effect of 11.3% and 7.5%, respectively, with no statistic significant difference from the control. This result demonstrates a synergistic effect of the mixed aqueous extracts from the two plants in terms of the increased analgesic effect, compared to the individual extracts.

EXAMPLE 6
Clinical Demonstration of Anti-inflammatory and Analgesic Effects of the Present Invention Mixed Aqueous Extracts 115 persons, 40 male and 75 female, with chronic gastritis, benign prostate hyperplasia, arthralgia, cervical disc, cystitis, degenerative joint arthritis, rheumatoid arthritis, tennis elbow, osteoportotic pain, migraine, diabetic neuropathy pain, and Rt. flank pain were administered the present invention mixed aqueous extracts for monitoring anti-inflammatory and analgesic effects. Every examined was administered any one of the preparations of Example 2 in a predetermined dose for 10 to 14 days. The doses of the preparations were defined as follows: each 2 tablets twice per day, each 10 ml of syrup three times per day, each one capsule twice per day, and each 3 ml of injection one time per day. After administration of 10 to 14 days, the therapeutic effects of the present invention mixed aqueous extracts are ranked as "aggravation", "no change", "slightly effective", "moderately effective" and "significantly effective" according to the recovery conditions. The examined were aged from 30 to 70.

The results are presented in Table 4.

TABLE 4

Clinical Results of the Present Invention Mixed Aqueous Extracts for Anti-inflammatory and Analgesic Effects.

| | Response | | | | | |
|---|---|---|---|---|---|---|
| | XX | X | ▽ | O | OO | Total |
| Chronic Gastritis | | 3 (37.5) | 1 (12.5) | 3 (37.5) | 1 (12.5) | 8 |
| Arthralgia | | 5 (35.7) | 2 (14.3) | 7 (50) | | 14 |
| Benign Prostate Hyperplasia | | | 1 (11) | 2 (22) | 6 (67) | 9 |
| Chronic and Recurrent Cystitis | | 1 (5) | 1 (5) | 7 (35) | 11 (55) | 20 |
| Cervical Disc | | 4 (23.5) | 8 (47) | 5 (29.4) | | 17 |
| Degenerative Joint Arthritis | | 3 (33.3) | 5 (55.6) | 1 (11.1) | | 9 |
| Rheumatoid Arthritis | | 1 (25) | 1 (25) | 2 (50) | | 4 |
| Tennis Elbow | | | 1 (16.7) | 3 (50) | 2 (33.3) | 6 |
| Osteoportotic Pain | | | | 6 (75) | 2 (25) | 8 |
| Rheumatoid Arthritis | | | | 2 (28.6) | 5 (71.4) | 7 |
| Diabetic Neuropathy Pain | | | | | 7 (100) | 7 |

TABLE 4-continued

Clinical Results of the Present Invention Mixed Aqueous Extracts for Anti-inflammatory and Analgesic Effects.

|  | Response | | | | | |
| --- | --- | --- | --- | --- | --- | --- |
|  | XX | X | ∇ | O | OO | Total |
| Rt. Flank Pain |  |  | 1 (16.7) | 5 (83.3) |  | 6 |

(Unit: person (%))

Response
XX: Aggravation
X: No Change
V: Slightly Effective
O: Moderately Effective
OO: Significantly Effective As shown in Table 4, the present invention mixed aqueous extracts were useful to 62.5% of people with chronic gastritis, 64.3% of people with arthralgia, 100% of people with benign prostate hyperplasia, 99% of people with chronic and recurrent cystitis, 76.4% of people with cervical disc, 66.7% of people with degenerative joint arthritis, 75% of people with rheumatoid arthritis, 66.7% of people with tennis elbow, 100% of people with osteoportotic pain, 100% of people with migraine, 100% of people with diabetic neuropathy pain, and 100% of people with Rt. Flank pain. Especially, the mixed aqueous extracts provided almost 100% anti-inflammatory and analgesic actions on the patients with benign prostate hyperplasia, chronic and recurrent cystitis, osteoportotic pain, migraine, diabetic neuropathy pain and Rt. Flank pain.

EXAMPLE 7

Toxicity Test $LD_{50}$ (the dose of a substance that is fatal to 50% of the test animals) was a very important value as an index indicating the acute toxicity of a drug in view of ascertaining the safety of the present invention mixed aqueous extracts of Anemarrhena Rhizoma and *Phellodendron amurense* RUPRECHT according to the present invention. The value of $LD_{50}$ was determined as follows.

30 normal ICR mice (male, 22±1 g) were divided into six groups A to E of 6 mice. Five groups of ICR mice were administered with five different doses of aqueous mixed aqueous extracts (5, 7.5, 10, 12.5 and 15 g/kg) prepared in Example 1 according to the present invention. 6 mice of group A were orally administered 5 g/kg body weight mixed aqueous extracts, 6 mice of group B 7.5 g/kg, 6 mice of group C 10 g/kg, 6 mice of group D 12.5 g/kg and 6 mice of group F 15 g/kg. The values of $LD_{50}$ were determined after administration according to the Behrens-Karber method. The results are presented in Table 5.

TABLE 5

Lethal Dose ($LD_{50}$) of the Present Invention Mixed Aqueous Extracts through Oral Administration

|  |  | P.O. Group | | |
| --- | --- | --- | --- | --- |
| Experimental Group | Dose (g/kg) | Number of Dead Animals/ Number of Examined Animals | * Z | ** d |
| A | 5 | 0/6 | — | — |
| B | 7.5 | 0/6 | 0 | 2.5 |
| C | 19 | 0/6 | 0 | 2.5 |

TABLE 5-continued

Lethal Dose ($LD_{50}$) of the Present Invention Mixed Aqueous Extracts through Oral Administration

|  |  | P.O. Group | | |
| --- | --- | --- | --- | --- |
| Experimental Group | Dose (g/kg) | Number of Dead Animals/ Number of Examined Animals | * Z | ** d |
| D | 12.5 | 0/6 | 0 | 2.5 |
| E | 15 | 0/6 | 0 | 2.5 |

* Z: 1/2 value of the number of dead animals with two successive doses.
** d: Difference of two successive doses.

As shown in Table 5, the mixed aqueous extracts were found to be a very safe drug to the body system, since the value of $LD_{50}$ was greater than 15 g/kg when the mixed aqueous extracts were orally administered in a high dose of 15 g/kg body weight. Namely, the present invention mixed aqueous extracts of Anemarrhena Rhizoma and *Phellodendron amurense* RUPRECHT can be administered in a safe way without toxicity to the body.

In addition, the examined animals used in measurement of $LD_{50}$ were necropsied and subjected to a pathobiological and histological test as follows. All survived animals were anaesthetized with ether and eviscerated to examine abnormalcy of organs through visual inspection. The examined organs were all held in 10% neutral formalin solution for 10 days or more, and subjected to dehydration and embedding in a paraffin embedding device (e.g., Fisher, Histomatic Tissue Processor, 166A). The organs were dissected into 5 μm fragments with a rotary microtome (e.g., AO Rotary Microtome) and dyed with hematoxylin and eosin.

Figure 4A:
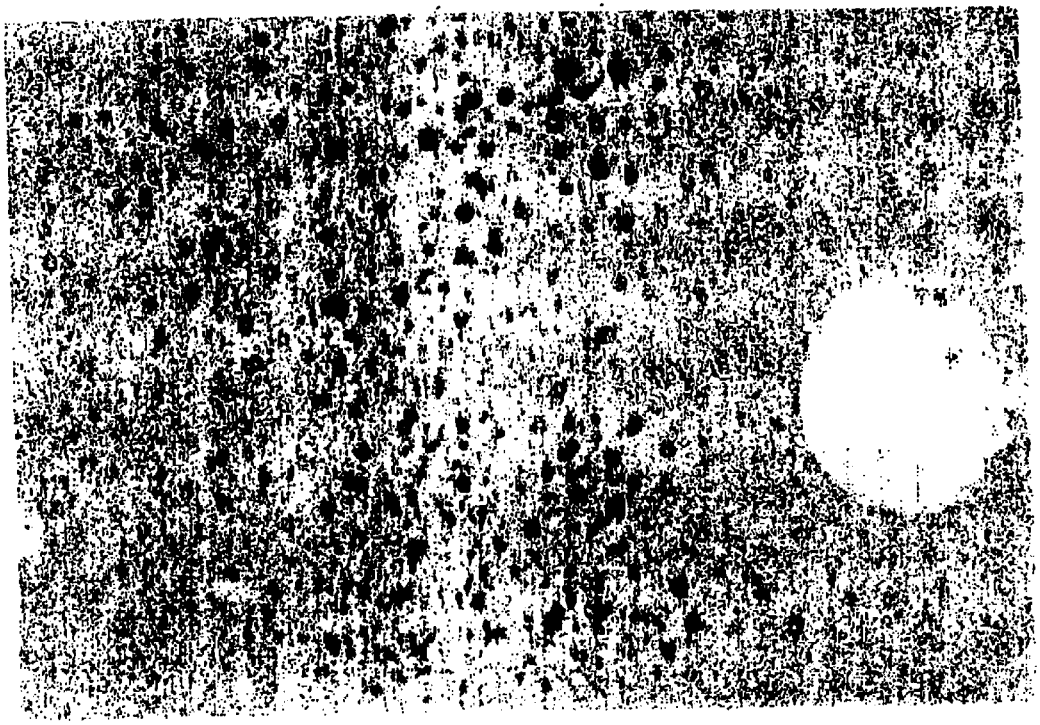
FIGS. 4a and 4b are photographs of liver X400 and kidney X200 of a mouse affected by the present invention mixed aqueous extracts of Anemarrhena Rhizoma and Phellodendron Bark.
Figure 4B:
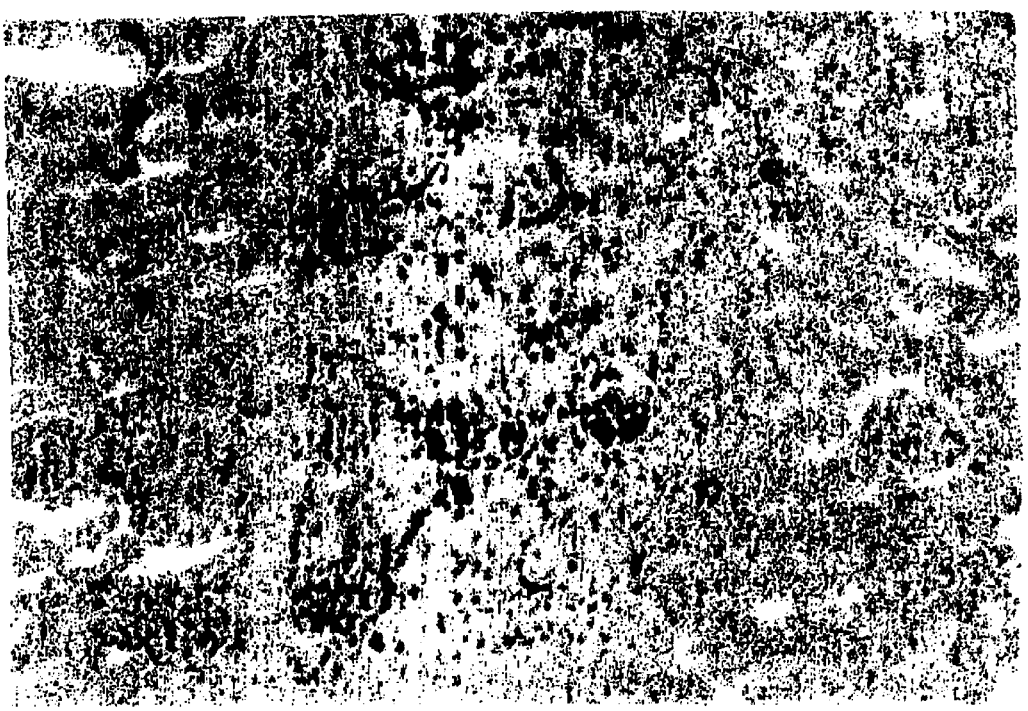

The pathological findings on the necropsied and H&E dyed animals were as follows. No drug-induced abnormalcy was observed in a liver tissue (FIG. 4a) and a kidney tissue (FIG. 4b) of the examined mice administered up to 15 g/kg body weight of the present invention mixed aqueous extracts. Further, no drug-induced abnormality appeared in myocardiac cells, stomach, intestinal track, pancreas, lung, spleen, adrenal gland, brain, testis, ovaries and bone marrow (not shown).

Consequently, it may be expected that the mixed aqueous extracts of Anemarrhena Rhizoma and *Phellodendron amurense* RUPRECHT according to the present invention can be administered in a dose of up to 15 g/kg body weigh, causing no side effect on all organs or providing no toxicity to damage the organs.

EXAMPLE 8

Figure 5:
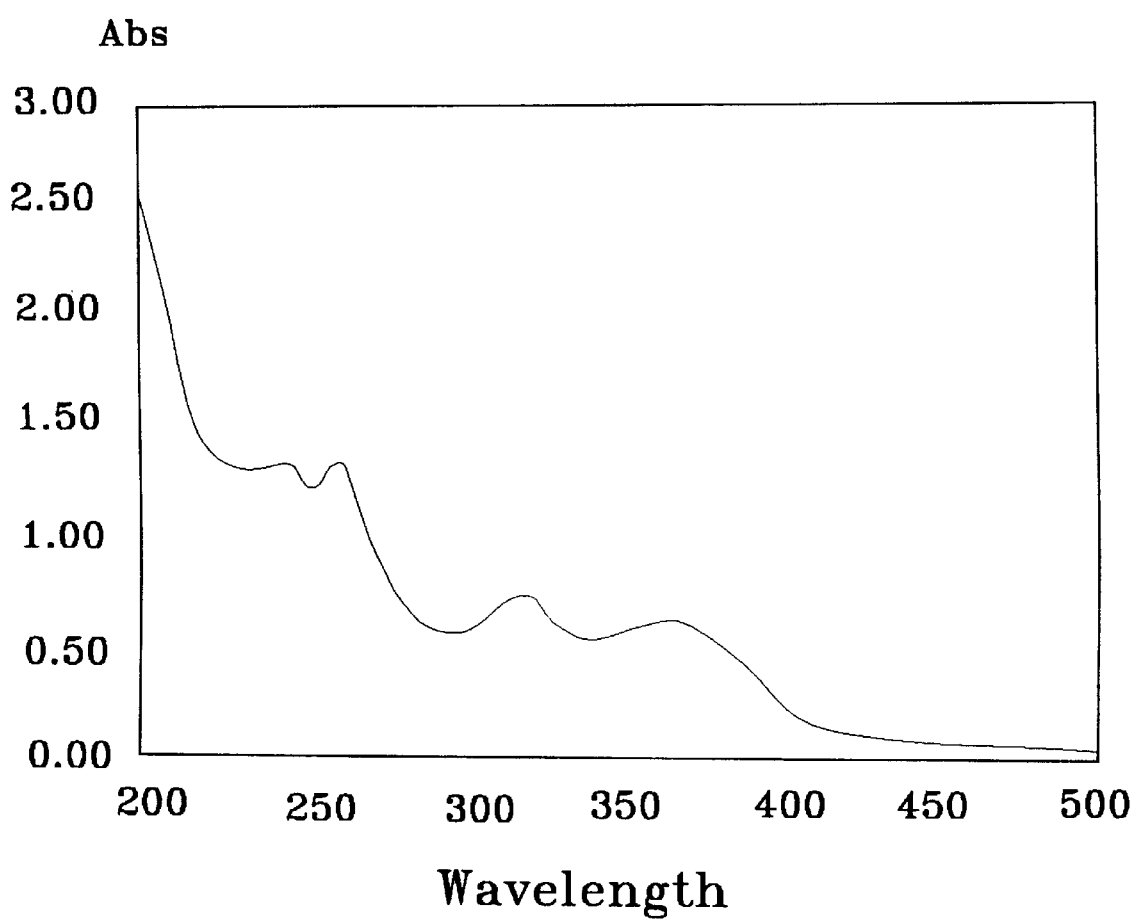
FIG. 5 is a UV spectrum of the single extract from Anemarrhena Rhizoma.
Figure 6:
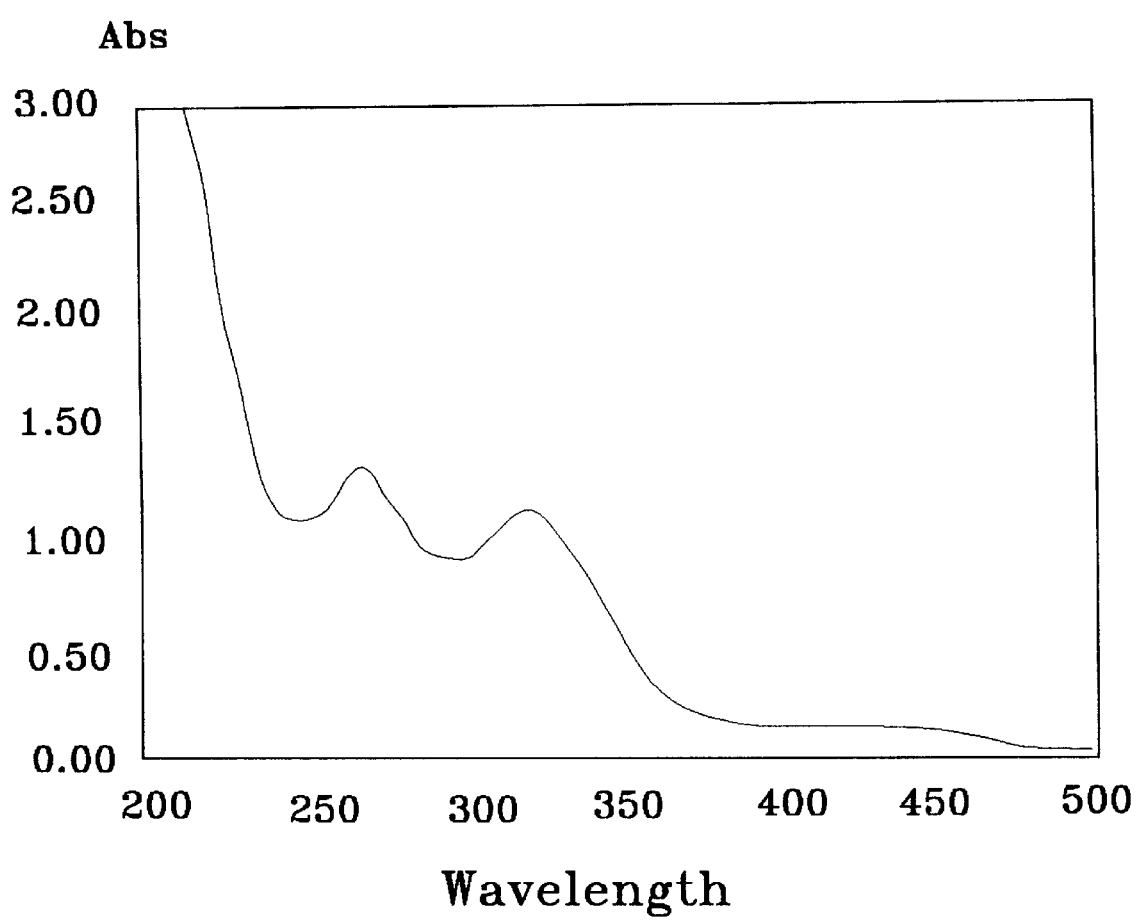
FIG. 6 is a UV spectrum of the single extract from Phellodendron Bark.
Figure 7:
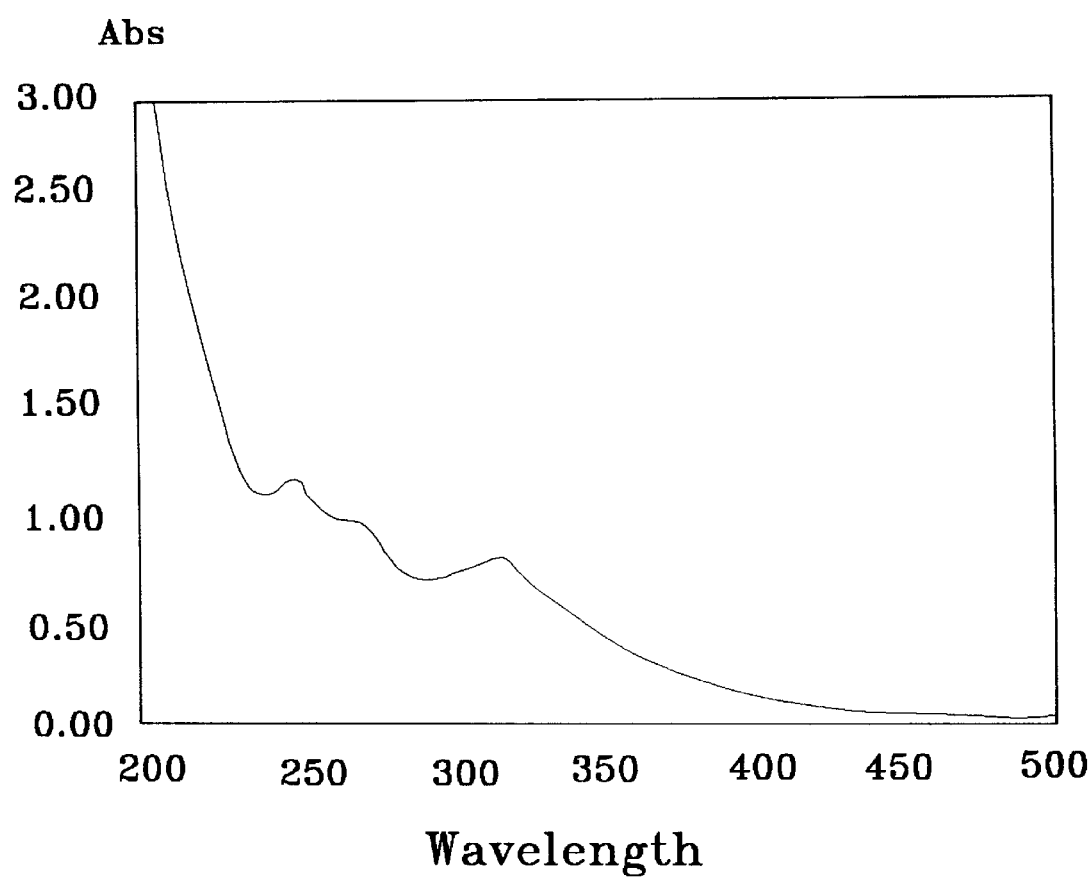
FIG. 7 is a UV spectrum of the present invention mixed aqueous extracts of Anemarrhena Rhizoma and Phellodendron Bark.

UV Spectrum Properties of the Present Invention Mixed Aqueous Extracts and Single Aqueous Extracts of *Phellodendron amurense* RUPRECHT and Anemarrhena Rhizoma An analysis was performed on single aqueous extracts obtained from *Phellodendron amurense* RUPRECHT and Anemarrhena Rhizoma, and a mixed extract thereof according to the present invention, using a UV spectrophotometer (Pharmacia, Ultrospec 2000). FIG. 5 shows a UV spectrum of the single aqueous extract from Anemarrhena Rhizoma (0.5 mg/ml), wherein the absorbance increases at 258, 316 and 365 nm. FIG. 6 shows a UV spectrum of the single aqueous extract from *Phellodendron amurense* RUPRECHT (0.25 mg/ml), wherein the absorbance rises at 278 and 325 nm. FIG. 7 shows a UV spectrum of the present invention mixed aqueous extracts of *Phellodendron amurense* RUPRECHT and Anemarrhena Rhizoma, wherein the absorbance increases at 258 and 317 nm.

EXAMPLE 9
HPLC Properties of the Present Invention Mixed Aqueous Extracts and Single Aqueous Extracts of *Phellodendron amurense* RUPRECHT and Anemarrhena Rhizoma An HPLC analysis was performed by dissolving single aqueous extracts obtained from *Phellodendron amurense* RUPRECHT and Anemarrhena Rhizoma, and mixed extracts thereof according to the present invention in water each in a concentration of 10 mg/ml. Each 10 µL of the resulting extract solutions was collected and analyzed with an HPLC (HP1090).

Figure 8:
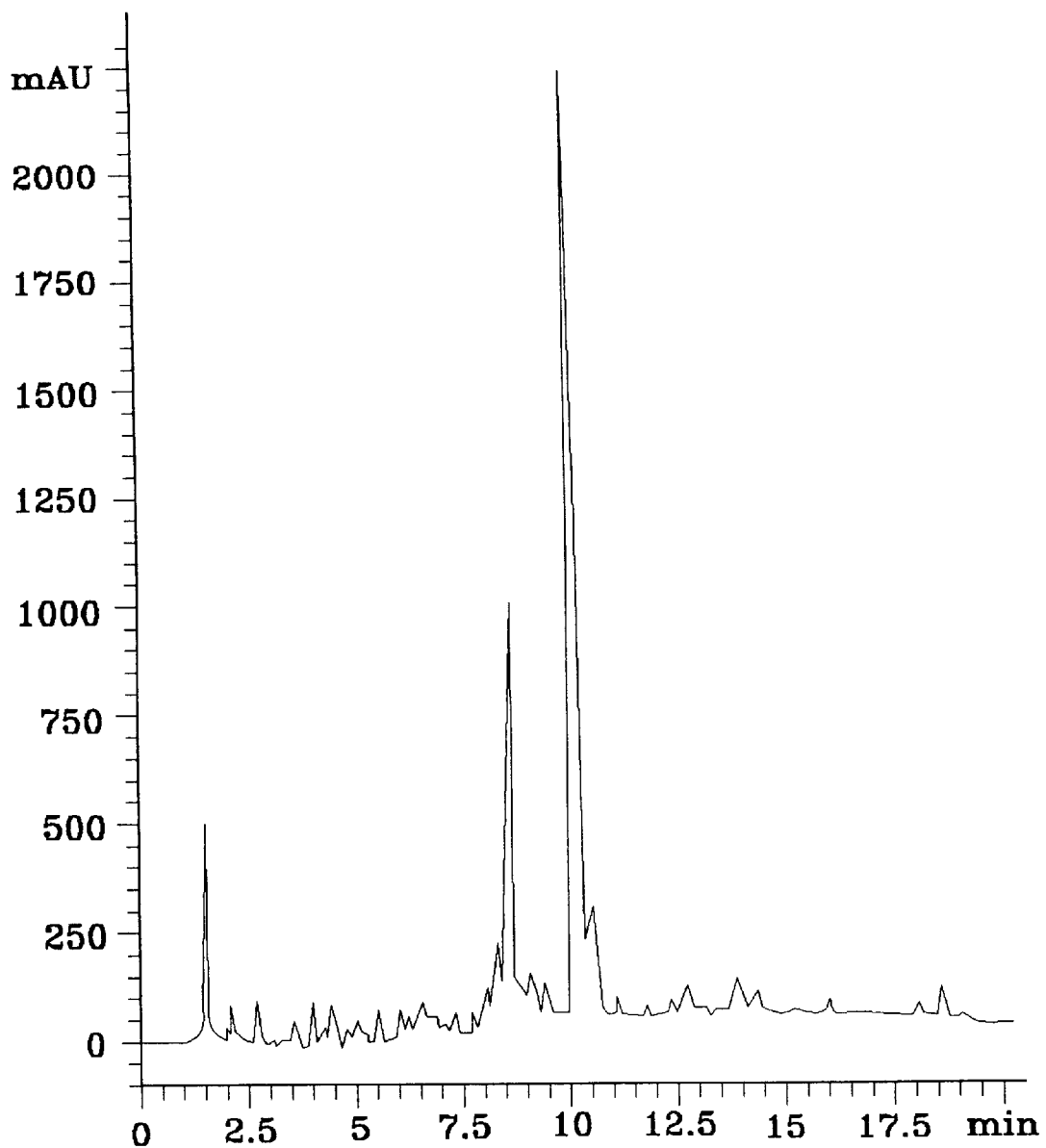
FIG. 8 is an HPLC chromatgram of the single aqueous extract from Anemarrhena Rhizoma.
Figure 9:
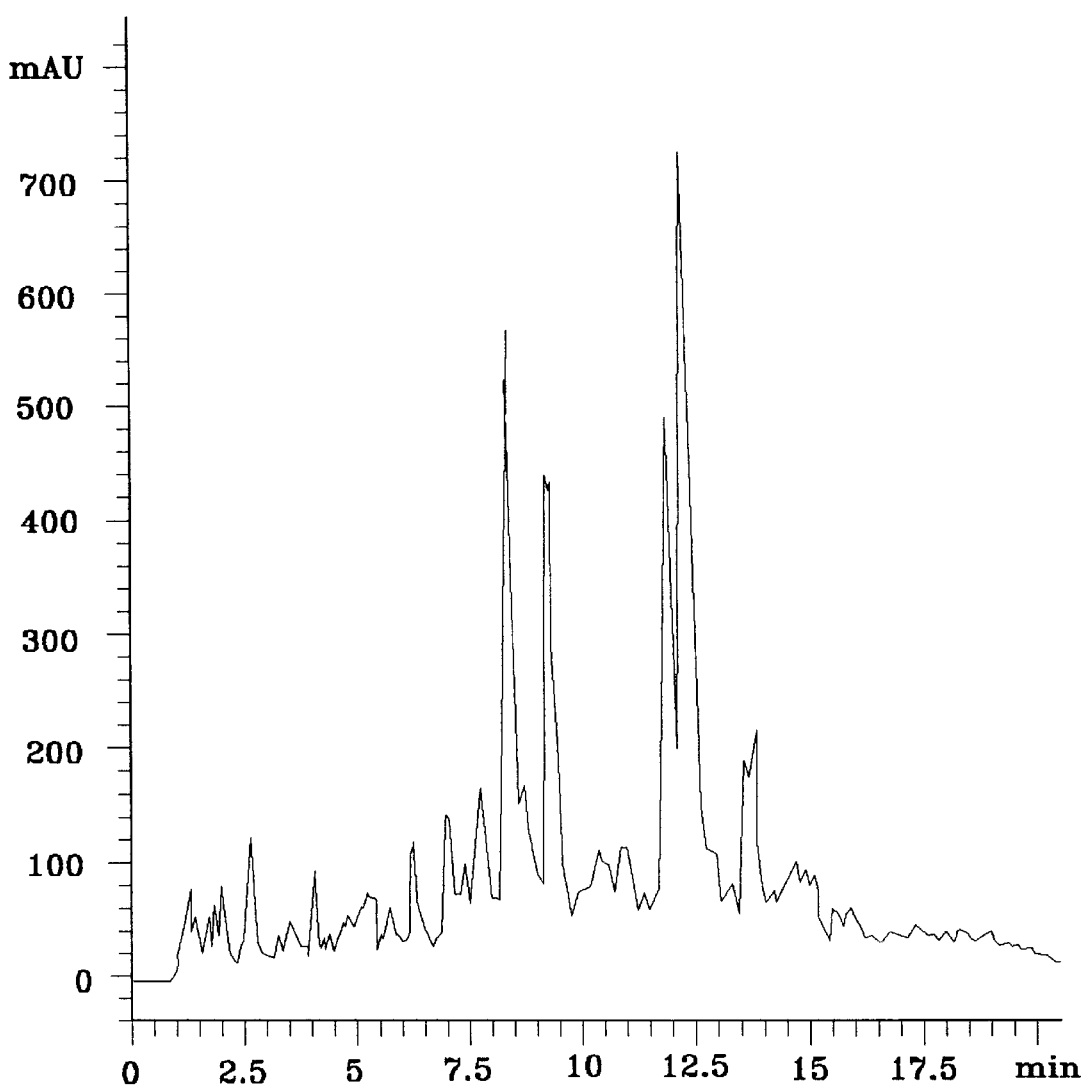
FIG. 9 is an HPLC chromatogram of the single aqueous extract from Phellodendron Bark.

(Analytical Conditions)
Column: C18 ODS; 4.6 mm i.d.×100 mmL
Mobile phase: gradient system of 1% acetic acid and methanol
Flow rate: 1 ml/min
Measurement: at 254 nm with photodiode array detector In the cyclic testing, unique peaks were observed in the respective extracts. FIG. 8 shows an HPLC profile of the single aqueous extract of Anemarrhena Rhizoma, with significant peaks at 1.097, 8.705 and 10.221 min., respectively. The peak at 1.097 min. is 2840.6±115.5 (average±standard deviation) in area and 508.7±15.5 high; the peak at 8.705 min. 10357.2±328.7 in area and 980.7±11.9 high; and the peak at 10.221 min. 30397.6±563.4 in area and 2181.4±17.5 high.

FIG. 8 shows an HPLC profile of the single aqueous extract of *Phellodendron amurense* RUPRECHT, wherein significant peaks appear at 7.817, 8.588, 10.126 and 10.381 min., respectively. The peak at 7.817 min. is 7600.9±115.5 in area and 511.1±15.5 high; the peak at 8.588 min. 4939.4±245.5 in area and 427.9±45.5 high; the peak at 10.126 min. 5115.8±325.5 in area and 458.2±35.5 high; and the peak at 10.381 min. 8524.8±529.5 in area and 702.2±35.5 high.

Figure 10:
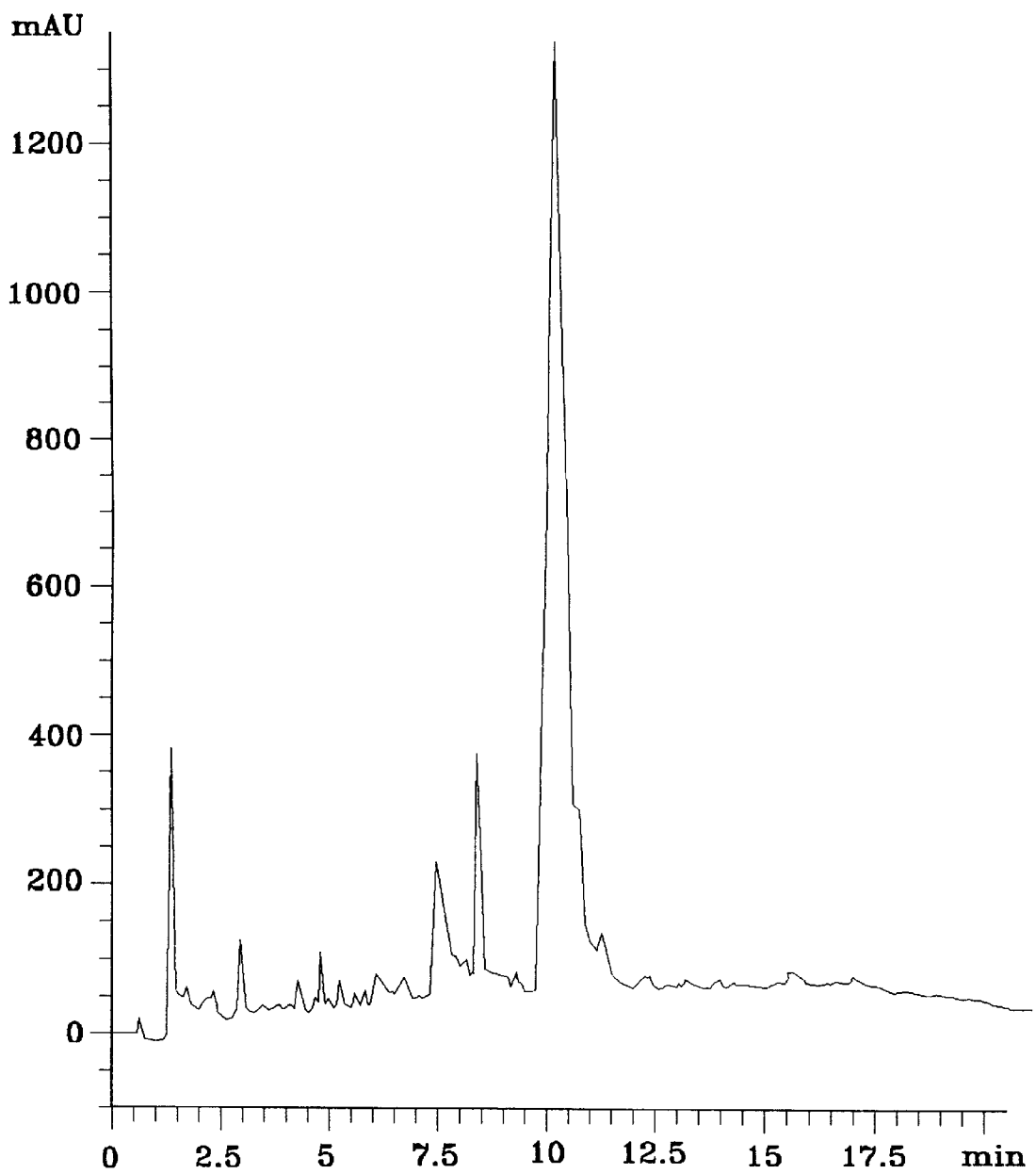
FIG. 10 is an HPLC chromatogram of the present invention mixed aqueous extracts of Anemarrhena Rhizoma and Phellodendron Bark.

FIG. 10 shows an HPLC profile of the mixed aqueous extracts of Anemarrhena Rhizoma and *Phellodendron amurense* RUPRECHT according to the present invention, wherein significant peaks appear at 1.055, 7.825, 8.600 and 10.146 min., respectively. It is estimated that the peak at 1.055 min is from Anemarrhena Rhizoma and the peak at 7.825 min is from *Phellodendron amurense* RUPRECHT. The peak at 1.055 min. is 1382.4±115.5 in area and 385.5±15.5 high, and the peak at 7.825 min. 2362.9±128.7 in area and 163.4±11.9 high.

EXAMPLE 10
TLC Properties of the Present Invention Mixed Aqueous Extracts and Single Aqueous Extracts of *Phellodendron amurense* RUPRECHT and Anemarrhena Rhizoma Thin layer chromatographic (TLC) methods were employed in analyzing constituents of single aqueous extracts obtained from *Phellodendron amurense* RUPRE-CHT and Anemarrhena Rhizoma, mixed aqueous extracts thereof according to the present invention, and standard materials, berberine and palmatine. A comparison of the results shows that the single aqueous extract of *Phellodendron amurense* RUPRECHT contains a large amount of berberine and palmatine and that the Anemarrhena Rhizoma does not contain alkaloids but saponins in a large amount. The present invention is also found to contain berberine and palmatine. The analytical conditions used in the present invention are presented below. The sample with alkaloids would turn orange under the following conditions.

(Analytical Conditions)
TLC aluminum sheet (20×20 cm): silica gel 60 $F_{254}$
Mobile phase: ethyl acetate:formic acid:water=90:5:5
Spray: $BiONO_3$+KI+acetic acid+water In summary, the present invention pharmaceutical composition for treatment of inflammation and pain is a crude extraction drug using mixed aqueous extracts of Anemarrhena Rhizoma and Phellodendron Bark, which produces less side effects and is suitable for long-period administration. The present invention does not lead to dependency or resistance.

The present invention is effective in normal inflammation and pain, for example, chronic gastritis, arthralgia, benign prostate hyperplasia, chronic and recurrent cystitis, cervical disc, degenerative joint arthritis, rheumatoid arthritis, tennis elbow, osteoportotic pain, migraine, diabetic neuropathy pain and Rt. Flank pain.

Especially, the present invention remarkable acts on benign prostate hyperplasia, chronic and recurrent cystitis, osteoportotic pain, migraine, diabetic neuropathy pain and Rt. Flank pain.

The present invention is a non-narcotic analgesic specific to peripheral tissues without a side effect.

The above-stated therapeutic effects of the present invention is much superior to those of the respective single aqueous extracts from Anemarrhena Rhizoma and Phellodendron Bark.

While the invention has been shown and described with reference to a certain preferred embodiment thereof, it will be understood by those skilled in the art that various changes in form and details may be made therein without departing from the spirit and scope of the invention as defined by the appended claims.

What is claimed is:

1. A pharmaceutical composition for treatment of inflammation and pain comprising an aqueous extract of a mixture of Anemarrhena rhizome and Phellodendron bark and a pharmaceutically accepted carrier, diluting ajents or excipients.

2. The pharmaceutical composition as claimed in claim 1, wherein the aqueous extract of a mixture of Anemarrhena rhizome and Phellodendron bark have an anti-inflammatory effect specific to a peripheral tissue or a non-narcotic analgesic effect.

3. The pharmaceutical composition as claimed in claim 1, wherein the inflammation and pain is selected from the group consisting of chronic gastritis, arthralgia, benign prostate hyperplasia, chronic and recurrent cystitis, cervical disc, degenerative joint arthritis, rheumatoid arthritis, tennis elbow, osteoporotic pain, migraine, diabetic neuropathy pain and right flank pain.

4. The pharmaceutical composition as claimed in claim 1, wherein the pharmaceutical composition comprises the aqueous extract obtained from a mixture of Anemarrhena rhizome and Phellodendron bark at a dry weight ratio of 1:0.2 to 1:5.

5. The pharmaceutical composition as claimed in claim 4, wherein the pharmaceutical composition comprises the aqueous extract obtained from a mixture of Anemarrhena rhizome and Phellodendron bark at a dry weight ratio of 1:0.5 to 1:2.

6. The pharmaceutical composition as claimed in claim 1, wherein the aqueous extract of a mixture of Anemarrhena rhizome and Phellodendron bark are formulated for oral administration in a daily dose of 10–50 mg/kg body weight of an adult.

7. The pharmaceutical composition as claimed in claim 1, wherein the aqueous extracts of a mixture of Anemarrhena rhizome and Phellodendron bark are formulated for injections in a daily dose of 20–100 mg based on 60 kg body weight of a person.

8. A method for preparing an aqueous extract of a mixture of Anemarrhena rhizome and Phellodendron bark comprising the steps of:
  a) extracting a mixture of Anemarrhena rhizome and Phellodendron bark with water and filtering the resulting extract to produce a filtrate;
  b) saturating said filtrate with water under a high pressure and removing coagulated proteins produced therein;
  c) adding an organic solvent to the filtrate and removing substances soluble in the organic solvent; and
  d) separating and freeze drying an aqueous layer to obtain the aqueous extract.

9. The method as claimed in claim 8, wherein in step a), the extracting water is added at a weight ratio of 1:10–45 with respect to the mixture of Anemarrhena rhizome and Phellodendron bark.

10. The method as claimed in claim 9, wherein in step a), the extracting water is added at a weight ratio of 1:25–35 with respect to the mixed aqueous extracts of Anemarrhena rhizome and Phellodendron bark.

11. The method as claimed in claim 10, wherein the organic solvent in step c) is chlroroform or hexane.

* * * * *